United States Patent [19]

Storz

[11] Patent Number: 4,641,634
[45] Date of Patent: Feb. 10, 1987

[54] ONE-HAND HYSTEROSCOPE

[76] Inventor: Karl Storz, AVF Dem Schildrain 39, 7200 Tuttlingen, Fed. Rep. of Germany

[21] Appl. No.: 731,649

[22] Filed: May 7, 1985

[51] Int. Cl.⁴ .............................................. A61B 1/00
[52] U.S. Cl. ..................................................... 128/4
[58] Field of Search ........................ 128/4, 5, 6, 7, 751

[56] References Cited

U.S. PATENT DOCUMENTS

| | | | |
|---|---|---|---|
| 1,127,948 | 2/1915 | Wappler | 128/7 |
| 3,368,552 | 2/1968 | Bottcher | 128/4 |
| 4,027,510 | 6/1977 | Hiltebrandt | 128/6 X |
| 4,372,295 | 2/1983 | Heckele | 128/6 X |
| 4,503,843 | 3/1985 | Boebel | 128/4 |

FOREIGN PATENT DOCUMENTS 509296 10/1930 Fed. Rep. of Germany.
2520223 7/1983 France.

Primary Examiner—William H. Grieb
Attorney, Agent, or Firm—Donald D. Mon

[57] ABSTRACT

The invention relates to a one-hand hysteroscope with a hysteroscope adapter for fixing by vacuum to the portio, in which the hysteroscope shaft and the viewing tube relative to the adapter can be advanced into the body cavity of the patient during hysteroscopy by one-handed operation.

To facilitate operation, for mounting the hysteroscope shaft in the hysteroscope adapter, an operating sleeve is provided, which is externally provided with notches for engagement of a movable forceps handle detent of one forceps half for a stepwise advance and which is arranged on the fixed sleeve bearing together with a fixed forceps half.

Thus, hand force need only be used when the stepwise advance on the optics takes place with visual observation. Automatic arresting of the optics in any random position is possible, without a given hand force having to be maintained.

The one-hand hysteroscope is intended for use in the medical field.

4 Claims, 5 Drawing Figures

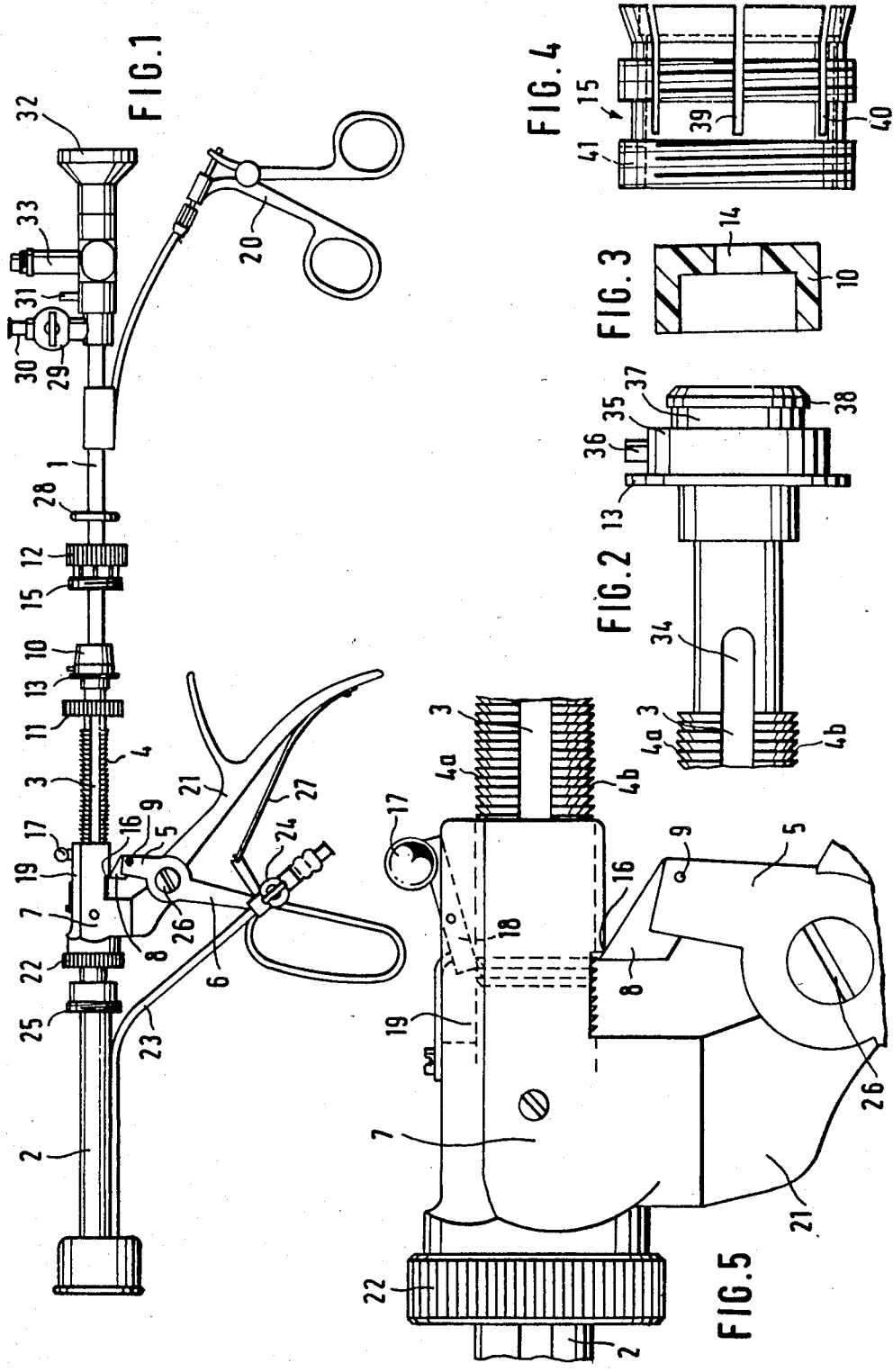

4,641,634

ONE-HAND HYSTEROSCOPE

FIELD OF THE INVENTION

The invention relates to a one-hand hysteroscope.

BACKGROUND OF THE INVENTION

During the inspection and operative treatment of the cervical canal and the uterine cavity by means of a hysteroscope, it is standard practice to operate the latter in a one-handed manner. The viewing tube is advanced into the uterine cavity against the tension of a spring, However, this leads to the serious disadvantage that the optical system under the longitudinal pressure must constantly be held in the desired position by exertion of the thumb against the spring tension, so that the endoscopic orientation is maintained. This is particularly critical when removing tissue, accompanied by the aid of biopsy forceps with optical viewing. It is known in this connection to place an auxiliary instrument such as biopsy forceps in the shaft or shank, in order to be able to take a tissue sample. The operation of the biopsy forceps rotates the end of the auxiliary instrument close to the patient.

The invention is based on the finding that it is of great importance for the hysteroscope optics to remain in precisely the desired position during a biopsy.

The invention is based on the problem of so improving the one-hand hysteroscope, that the operation is significantly facilitated. In particular, there is to be a stepwise advance of the optics, together with an arresting thereof in any random position and in an automatic manner, without it being necessary to maintain a specific hand force. It must also be possible to use hysteroscope shafts with different diameters.

BRIEF DESCRIPTION OF THE INVENTION

A one-hand hysteroscope according to this invention includes a sleeve bearing in which an operating sleeve is longitudinally slideable. One forceps half is rigidly mounted to the sleeve bearing, and another is pivotally mounted to it so the surgeon can squeeze the two toward one another to advance the operating sleeve in the bearing. The sleeve includes a sequence of notches. A drive pawl is moved by the pivoted forcep half to engage the notches and drive the sleeve forwardly. Because it is a pawl, the reverse movement of the forcep half releases the pawl from the notches and enables the pivoted forceps half to return for another incremental advance. A spring latch mounted to the sleeve bearing engages the notches to restrain the sleeve from reverse movement unless the latch is released.

BRIEF DESCRIPTION OF THE DRAWINGS

The invention is described in greater detail hereinafter relative to a non-limitative embodiment and the attached drawings, in which:

FIG. 1 is a side view of the complete hysteroscope with a disengaged sealing screw coupling.

FIG. 2 is a side view of a detail of FIG. 1.

FIG. 3 shows a the sealing cap according to FIG. 1.

FIG. 4 shows a the rubber cap sleeve according to FIG. 1.

FIG. 5 is a partial view of the instrument according to FIG. 1 on a larger scale.

DETAILED DESCRIPTION OF THE INVENTION

In the case of the one-hand hysteroscope according to FIG. 1, it is possible to see at the end close to the patient at the left the hysteroscope adapter 2 for fixing by vacuum to the portio. This vacuum is provided by a vacuum duct connected by tap 24 to the vacuum pump or syringe. It is possible to use several sizes of said adapter with different bores and an examination or operation shaft or shank 1. Further to the right, it is possible on adapter 2 to see a threaded collar 25, which is used for attachment to the sleeve bearing 7 by means of cap nut 22.

The rigid forceps half 21 is fixed to the sleeve bearing 7. The pivotal the forceps half 6 can be pivoted about screw 26 fixed to the rigid half. Between the two forceps halves 21 and 6 there is a spring mechanism of a known construction, which forces apart the forceps halves when not squeezed together.

Above the shaft bearing 19 there is a button 17, which is mounted on a locking lever 18, which is shown in FIG. 5. Beneath this there is provided a movable forceps handle detent, provided with a movable engagement member 8, as will be explained hereinafter.

Operating sleeve 3 projects to the right from bearing 19 and on it is rotatably provided a cap nut 11, which is knurled. Further to the right there is provided a stepped disk 13, which is secured to the operating sleeve 3 and receives a rubber seal 10, as will be explained hereinafter. Further to the right it is possible to see the rubber cap sleeve 15, together with another cap nut 12, which serves to screw down the seal 10. This also applies to disk 28, which is shown further to the right on shaft 1.

Further to the right at the end (closer to the patient) of the hysteroscope shaft 1, there is provided a conventional connection 30 to a tap 29 for gas insufflation or for instillation of liquids. Finally, to the far right, there is a shutter 31 for the optics, whose eyepiece 32 is visible and at the top there is a connection 33 for the light guide.

Hysteroscopes of this general type are known to the expert and consequently need not be described in detail. Hereinafter, only those parts will be described, which are novel compared with the prior art and essential to the invention.

FIG. 2 shows only that part of the operating sleeve 3 according to FIG. 1 which is provided in the bearing 9 for the axial displacement of the hysteroscope shaft 1.

At the top, sleeve 3 has sawtooth notches 4a and at the bottom similar notches 4b, which are separated from one another by a guide groove 34. Thus, further to the right, it is possible to see the stepped disk 13, whose left-hand diameter is at a maximum. This is followed to the right by part of disk 35 having a smaller diameter and which is provided at the top with a pin 36. This is followed to the right by a part 37 having a still smaller diameter and having at the far right a bead 38.

FIG. 3 shows in section a sealing cap 10, which can be mounted on part 37. There is a central hole 14, which has a diameter relative to the hysteroscope shaft, such that the latter can pass through it.

FIG. 4 shows a rubber cap sleeve 15 with a few longitudinal slots 39, 40, whilst there is a groove 41 for receiving pin 36. Slots 39, 40 are provided to make the rubber cap sleeve even more elastic. Sleeve 15 is passed over the rubber seal 10 until it strikes against disk 13.

FIG. 5 shows the sleeve bearing 7 with the aforementioned operating sleeve 3, which is used for receiving the hysteroscope or endoscope shaft 1, which is not shown here. To the left, there is once again the adapter 2, which is screwed onto the sleeve bearing 7 by means of a knurled cap nut 22. Below it, it is possible to see part of the fixed forceps half, in which is fixed by means of screw 26 the movable forceps half 6 according to FIG. 1. Forceps handle detent 5 is provided at the top with a spring-loaded engagement member 8, (sometimes called a pawl) which can be pivoted about joint 9. The spring for actuating the engagement member is not shown here, but is located in detent 5.

Also, sleeve bearing 7 is provided with a stop 16, against which the engagement member strikes in such a way that it does not engage in notches 4b in this inoperative position. This is important, so that the operating sleeve 3 can be retracted to the right in this position, when button 17 at the top of sleeve bearing 7 is forced downwards. Then, the spring-loaded locking lever 18 is pivoted about its pivot bearing 19 out of engagement with notches 4a. Locking lever 18 is shown only in broken line form, because it is not in fact visible. The lever is biased toward its illustrated locked position, perhaps by a leaf spring.

The operation of the hysteroscope of the invention will now be described. In the inoperative position shown in FIGS. 1 and 2, the two forcep halves 6 and 21 are biased apart by spring 27, so that the engagement member 8 is disengaged with respect to the sawtooth notches 4b. If the surgeon now operates the movable forceps half 6 with one hand, the forceps handle detent 5 is forced to the left and engages with the sawtooth notches 4b. On further operation, the operating sleeve 3 is forced in stepwise manner to the left, together with shaft 1. Locking lever 18 engages in spring-loaded manner in the sawtooth notches 4a, so that no sliding back of the operating sleeve 3 is possible. However, spring means 27 enables the forceps half 6 to move back again, because the pivotable, spring-loaded engagement member 8 gives way and slides back over notch 4b. On operating the forceps, it is consequently possible to have a stepwise advance of operating sleeve 3 and therefore shaft 1, so that through the locking lever, there is an arresting action to the rear.

Thus, without operating the instrument, the surgeon can be sure that the hysteroscope shaft with the viewing tube does not slide back when no hand force is exerted.

If the hysteroscope shaft is now to be retracted, it is merely necessary to press button 17 downwards, so that the sleeve 3 can move to the rear and can be manually removed up to a stop.

During observation, auxiliary instrument 20 can be operated in known manner which is made even easier by the invention, because the surgeon does not have to exert any hand force when the hysteroscope shaft is stationary. Thus, e.g. tissue can be removed from the observed point by means of the represented biopsy forceps 20.

Another advantage attainable by the invention is that hysteroscope shafts of different sizes for investigation or operation purposes can be interchanged in the operating sleeve 3 according to the invention by means of the seal according to FIGS. 2 to 4.

This invention thereby provides a hysteroscope which, with one hand, enables the operating sleeve to be advanced incrementally by squeezing on the handles. It will hold its advanced position until lever 18, operating as a spring-biased latch, is released. Engagement member 8 operates as a pawl, which engages a notch when driven forwardly, and releases when it returns.

What is claimed is:

1. A one-hand hysteroscope comprising: a sleeve bearing; an operating sleeve having an axis, and being axially movable in said sleeve bearing; a rigid forceps half rigidly mounted to said sleeve bearing; a pivoted forcep half pivotally mounted to said sleeve bearing; a plurality of notches arranged in axial sequence along the exterior of said operating sleeve; a pawl mounted to said rotatable forceps half, adapted to engage one of said notches and advance the operative sleeve in a forward direction when the forceps halves are moved toward one another, and to retract from the notches when they are moved apart from one another; and latch means mounted to said sleeve bearing and releasably engageable with said notches to restrain the operating sleeve from movement in the reverse direction unless released.

2. A one-hand hysteroscope according to claim 1, wherein the notches are sawtooth-shaped.

3. A one-hand hysteroscope according to claim 1 in which said pawl is a pivoted engagement member pivotally mounted to said pivoted forceps half, in which said sleeve bearing includes means to remove said engagement member from said notches when the forceps halves are released, and in which said engagement member is biased toward said notches, and said forceps halves are biased apart.

4. A one-hand hysteroscope according to claim 1, wherein the operating sleeve has a rubber seal on the end remote from the patient, so that hysteroscope shafts of different sizes can be used.

* * * * *